US00PP16294P3

(12) United States Plant Patent
Ishii et al.

(10) Patent No.: US PP16,294 P3
(45) Date of Patent: Feb. 28, 2006

(54) BUNASHIMEJI MUSHROOM PLANT NAMED 'HOKUTO SHIRO ICHIGOUKIN'

(50) Latin Name: *Hypsizygus marumoreus*
Varietal Denomination: Hokuto Shiro Ichigoukin

(75) Inventors: Makoto Ishii, Nagano (JP); Hisae Imai, Nagano (JP); Mizue Yamazaki, Nagano (JP)

(73) Assignee: Hokuto Sangyo Kabushiki Kaisha, Nagano (JP)

( * ) Notice: Subject to any disclaimer, the term of this patent is extended or adjusted under 35 U.S.C. 154(b) by 32 days.

(21) Appl. No.: 10/624,520

(22) Filed: Jul. 23, 2003

(65) Prior Publication Data

US 2004/0025215 P1 Feb. 5, 2004

(30) Foreign Application Priority Data

Jul. 23, 2002 (JP) ..... 14858

(51) Int. Cl.
*A01H 15/00* (2006.01)

(52) U.S. Cl. ..... Plt./394
(58) Field of Classification Search ..... Plt./394
See application file for complete search history.

(56) References Cited

FOREIGN PATENT DOCUMENTS

| | | |
|---|---|---|
| JP | 05-252842 | 10/1993 |
| JP | 09-140285 | 6/1997 |
| JP | 11-187780 | 7/1999 |
| JP | 2002-369635 | 12/2002 |

*Primary Examiner*—Kent Bell
(74) *Attorney, Agent, or Firm*—Armstrong, Kratz, Quintos, Hanson & Brooks, LLP

(57) ABSTRACT

The present variety of mushroom plant named 'Hokuto Shiro Ichigoukin' was produced by crossbreeding mutant fungal strains of two parent varieties, a + variety 'Hokuto Hachigoukin' and a – variety 'Hokuto Jyunigoukin,' after UV irradiation. This edible mushroom is not bitter, and can be cultivated anywhere a cultivation facility can be arranged.

12 Drawing Sheets

Latin name of the genus and species of plant claimed: *Hypsizygus marumoreus.*

The present plant patent application claims priority of Japanese plant variety application No. 14858, filed Jul. 23, 2002, which is hereby incorporated by reference.

'Hokuto Shiro Ichigoukin' is a variety of Bunashimeji mushroom plant that was produced by improving the existing varieties to have the following properties: nice white color, no bitter taste, delicious taste with a higher saccharide content, and cultivatable under similar conditions, including cultivation cycle. The scientific name of the variety is *Hypsizygus marumoreus.* The present plant is an edible mushroom.

BACKGROUND OF THE INVENTION

The present variety 'Hokuto Shiro Ichigoukin' was produced using mutant fungal strains of two parent varieties, 'Hokuto Hachigoukin' (unpatented) and 'Hokuto Jyunigoukin' (unpatented), grown by Hokuto Sangyo Kabushiki Kaisha. Specifically, the + variety was 'Hokuto Hachigoukin' and the – variety was 'Hokuto Jyunigoukin'. 'Hokuto Hachigoukin' and 'Hokuto Jyunigoukin' were each submitted to UV irradiation, and then the mutated varieties were crossbred to produce the present variety 'Hokuto Shiro Ichigoukin'.

The site of development was on property of Hokuto Sangyo Kabushiki Kaisha Kinoko Sougo Kenkyusho in Nagano, Japan.

In April 2000, the mutated 'Hokuto Hachigoukin' was produced, in that a UV-irradiated strain was spawned on a culture medium. In August 2000, the mutated 'Hokuto Hachigoukin' was harvested, and monospores were isolated.

In parallel, in May 2000, the mutated 'Hokuto Jyunigoukin' was produced, also in that a UV-irradiated strain was spawned on a culture medium. In October 2000, the mutated 'Hokuto Jyunigoukin' was harvested, and monospores were isolated.

In September and October 2000, primary hyphae were obtained from mutated 'Hokuto Hachigoukin' and mutated 'Hokuto Jyunigoukin'. From December 2000, mutated 'Hokuto Hachigoukin' and mutated 'Hokuto Jyunigoukin' were used to obtain crossbred stains. In February 2001, cultivation was started, and harvesting began in May 2001.

For cultivation, the cultivated hyphae are typically inoculated in a cultivation medium, like potato dextrose agar (PDA), filled in a sterilized cultivating dish for cultivation and subjected to treatment for growing the mushroom.

Further, in June 2001, a cultivation test was started for secondary selection. In October 2001, an HM222 strain, which appeared to be a superior variety, was selected. In December 2001, a cultivation test was initiated for stabilization.

In January 2002, a characteristic test was started. In May 2002, after repeated cultivation tests, stability, reproducibility and homogeneity, matching the objectives of improvements, were confirmed, i.e., the asexually propagated clones of the present plant are identical to the original plant in all distinguishing characteristics. Thus the HM222 strain was named 'Hokuto Shiro Ichigoukin'.

SUMMARY OF THE INVENTION

The present invention provides a variety, 'Hokuto Shiro Ichigoukin', which is an edible mushroom. When this mushroom is cooked in hot water, the bitterness associated with bunashimeji is mostly gone, thus making it a delectable variety. The present variety can be cultivated anywhere a cultivation facility can be arranged.

In summary, the morphological characteristics of 'Hokuto Shiro Ichigoukin' are as follows: at the appropriate harvesting period, the cap is small and round; the color of the cap center and margin is white; the thickness and quality of the cap meat are medium; the number of mottled spots is medium; the mottled spots are distributed in the central area; the clarity of the mottled spots is medium; the color of the gills is yellowish white; the arrangement of the gills is orderly; the width and density of the gills are medium; the length of the stipe is medium; attachment of the stipe to the cap is centric; the shape of the stipe is moderately thick; the color of the stipe is white; there is no hair on the stipe; and the quality of the stipe meat is medium.

As to the cultivation data for 'Hokuto Shiro Ichigoukin', yield is about 118.5 g, the number of effective fruit bodies is 62, and the length of time from spawning to harvesting is 91 days.

BRIEF DESCRIPTION OF THE DRAWINGS

FIGS. 8A and 8B show the state in which fungal hyphae of the present invention and a comparison variety, 'Miyuki M-8171' confront each other in a single dish. These fungal hyphae doe not commingle, forming a boundary line. This indicates that the two varieties are genetically different from each other. FIG. 8B is a bottom view of the dish shown in FIG. 8A for providing a much better understanding of the boundary line;

FIG. 9A represents growth rates of the fungal hyphae cultivated in the range of 22° C. to 30° C.

DETAILED DESCRIPTION OF THE INVENTION

Figure 1:
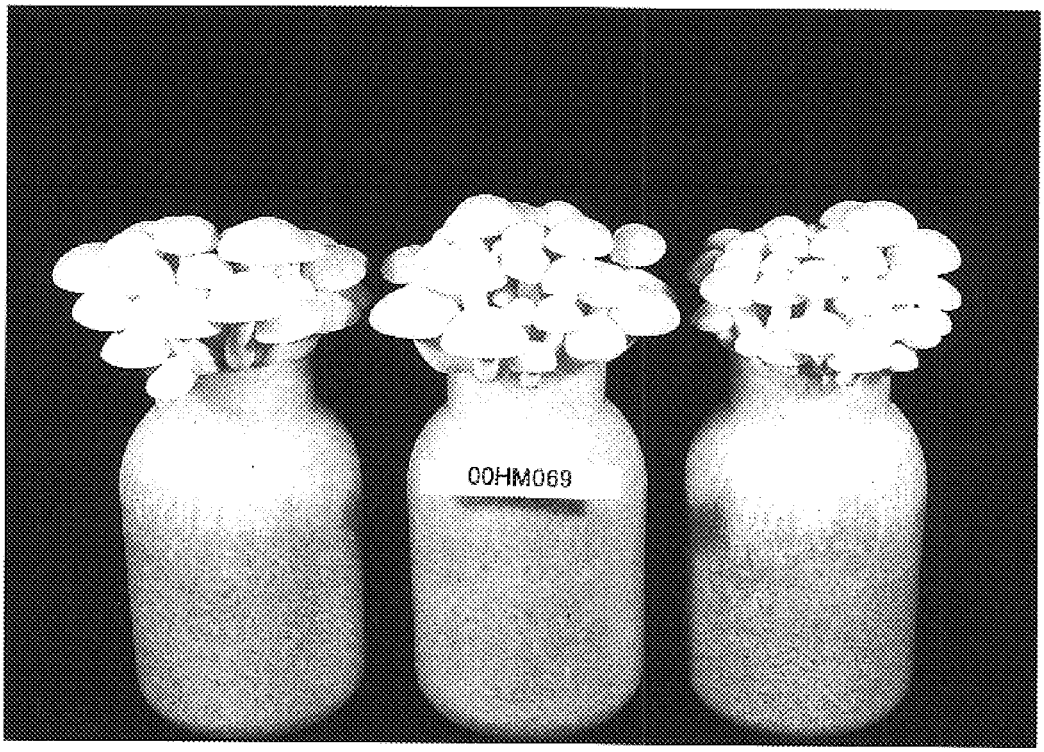
FIG. 1 is a photograph showing a front view of the present plant variety cultivated in vases. The test number designation 00HM069 was used before assignment of the variety name.
Figure 2:
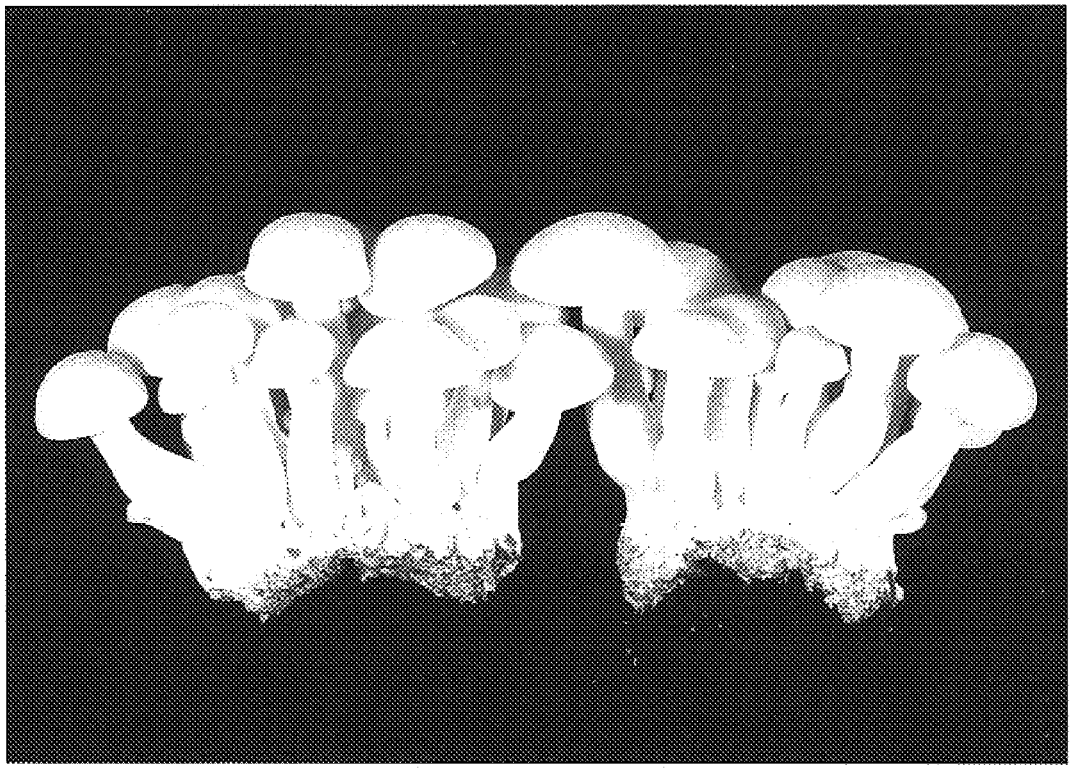
FIG. 2 is a photograph showing a front view of the present variety without growth substrate.
Figure 3:
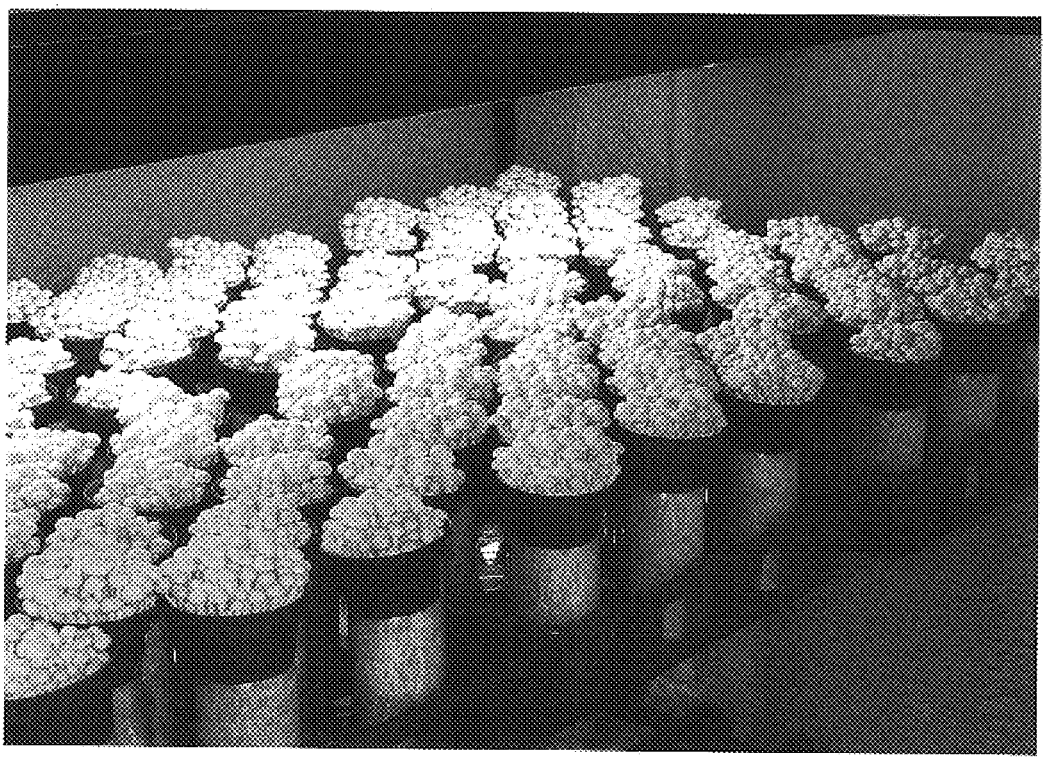
FIG. 3 is a photograph showing a perspective view of the present plant variety cultivated in vases.

The characteristics of the present variety will be described in comparison with one of the parent varieties. 'Hokuto Hachigoukin', and with another corresponding variety, 'Muyiki M-8171', which is commercially available (samples were bought at a supermarket in Nagano, Japan).

The cultivation site for this comparison was Hokuto Sangyo Kabushiki Kaisha in Nagano, Japan. The cultivation period was January to June 2002. The cultivation was made according to the conventional methods in a facility with a culture room of approximately 60 $m^3$ in size and a growth room of approximately 30 $m^3$ in size. In both the culture and growth rooms, an air-conditioning unit, comprising a cooler and heat exchanger, was installed, and in the growth room, cultivation racks and lights were placed. For characteristic analyses, three cultivation tests were performed using 25 bottles per block. The cultivation method used nutrient propagation, and strains were used as seeds.

In summary, when compared to 'Hokuto Hachigoukin', 'Hokuto Shiro Ichigoukin' exhibits the following characteristics: formation of an inhibition zone in dual culture; dense aerial hyphae ('Hachigoukin': medium density); cross sectional shape of hat is umbonate ('Hachigoukin': umbonate to flat); white cap center ('Hachigoukin': yellowish brown); white cap margin ('Hachigoukin': light grayish brown); medium quantity of mottled spots ('Hachigoukin': many); central distribution of mottled spots ('Hachigoukin': all areas except margin); yellowish white colored gills ('Hachigoukin': white); and medium length stipe ('Hachigoukin': long).

When compared to the commercial variety, 'Hokuto Shiro Ichigoukin' exhibits the following characteristics: formation of an inhibition zone in dual culture; dense aerial hyphae (commercial variety: medium density); clumped pattern for fruit body development (commercial variety: grouped pattern); central distribution of mottled spots (commercial variety: all areas except margin); yellowish white colored gills (commercial variety: white); a diameter under cap to maximum diameter ratio of 1.59 (commercial variety: 1.6–1.8); and a cap diameter to stripe length ratio of ≧2.1 (commercial variety: 1.5–2.0).

In brief the Reference Table below summarizes some of the dimensions of the present invention as compared to the parent varieties, Hokuto Hachigoukin and Hokuto Jyunigoukin, as well as the comparison variety Miyuki M-8171.

Reference Table
(Dimensions of typical variety of the invention)

| | Hokuto Shiro Ichigoukin | Hokuto Hachigoukin | Miyuki M-8171 | Hokuto Jyunigoukin |
|---|---|---|---|---|
| Cap Diameter (mm) d1 | 23.2 | 23.4 | 24.9 | 22.5 |
| Stipe Length (mm) L | 49.3 | 56.9 | 41.5 | 55.7 |
| Ratio (L/d1) | 2.13 | 2.45 | 1.68 | 2.48 |
| Stipe Diameter just beneath Cap (mm) | 7.42 | 5.86 | 7.80 | 7.29 |
| Maximum Stipe Diameter (mm) | 11.79 | 9.21 | 13.27 | 9.58 |
| Ratio (d3/d2) | 1.59 | 1.58 | 1.71 | 1.31 |
| Cap Thickness (mm) | 8.0 | 6.8 | 7.4 | 8.2 |

The relationship between the parental varieties 'Hokuto Hachigoukin' and 'Hokuto Jyunigoukin' is explained below: 'Hokuto Hachigoukin' has a cap (pileus) with a taupe-color center. 'Hokuto Jyunigoukin' is deep gray brown in color. The rim portion of the cap of 'Hokuto Hachigoukin' is pale gray brown, and that of 'Hokuto Jyunigoukin' is gray brown in color. The cap of 'Hokuto Jyunigoukin' is deeper in color on the whole in comparison with 'Hokuto Hachigoukin'. Maculae are distributed over the entire cap of 'Hokuto Hachigoukin', but those of 'Hokuto Jyunigoukin' are concentrated at the central part of the cap. The stem of 'Hokuto Hachigoukin' is white, but that of 'Hokuto Jyunigoukin' is somewhat yellowish in color. Thus, these strains can readily be distinguished in the process of cultivating the strains.

The characteristics of the present plant variety will now be described in details, with relevant comparisons with varieties 'Hokuto Hachigoukin' and 'Miyuki M-8171'.

(1) Dual culture

The test was done according to the examination standards established for Shirotamogitake (*Hypsizygus ulmarius*). With regard to the inhibition zone, the results were shown in Table 1 below (+: inhibition zone, –: no inhibition zone formation).

TABLE 1

| Inhibition Zone | | | |
|---|---|---|---|
| Similar variety | "Hokuto Shiro Ichigoukin" | "Hokuto Hachigoukin" | "Miyuki M-8171" |
| "Hokuto Shiro Ichigoukin" | – | + | + |

Thus, an inhibition zone was formed between 'Hokuto Shiro Ichigoukin' and the comparative varieties 'Hokuto Hachigoukin' as well as 'Miyuki M-8171', which is the closest variety after 'Hokuto Hachigoukin'.

Figure 4A:
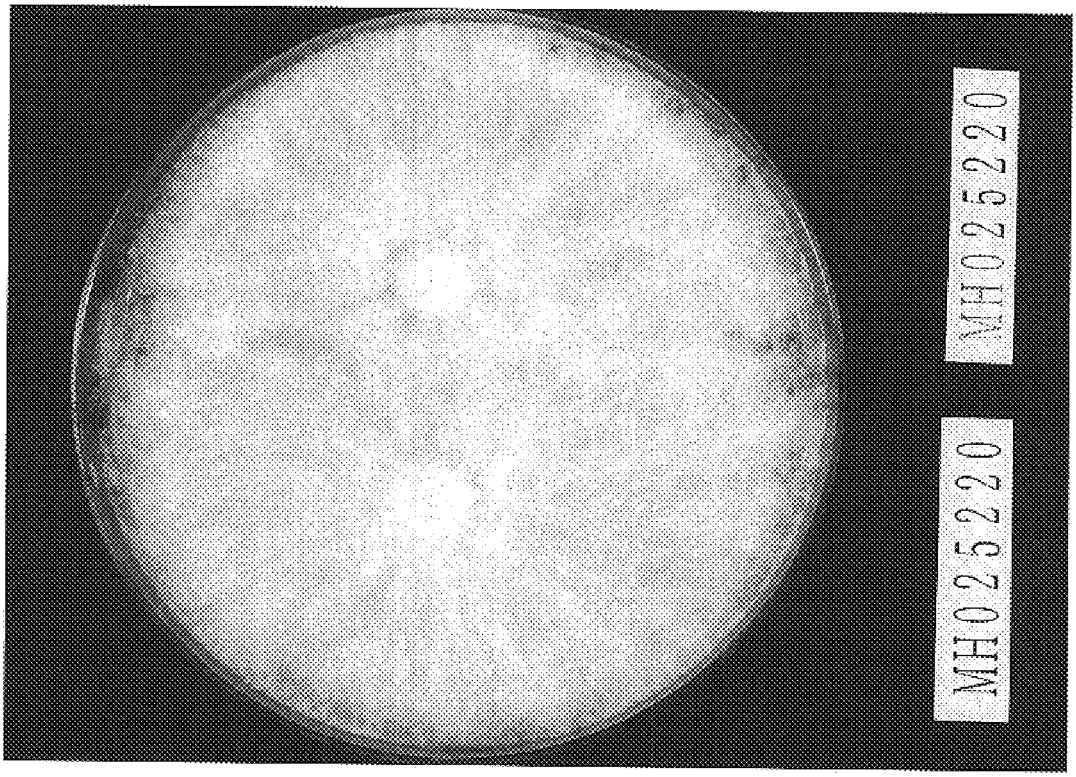
FIGS. 4*a* and 4*b* are photographs showing a surface and a back, respectively, of a culture of the present plant variety. In these figures, the designation MH025220 is the inventor's company's internal designation for the stock culture of 'Hokuto Shiro Ichigoukin'.
Figure 4B:
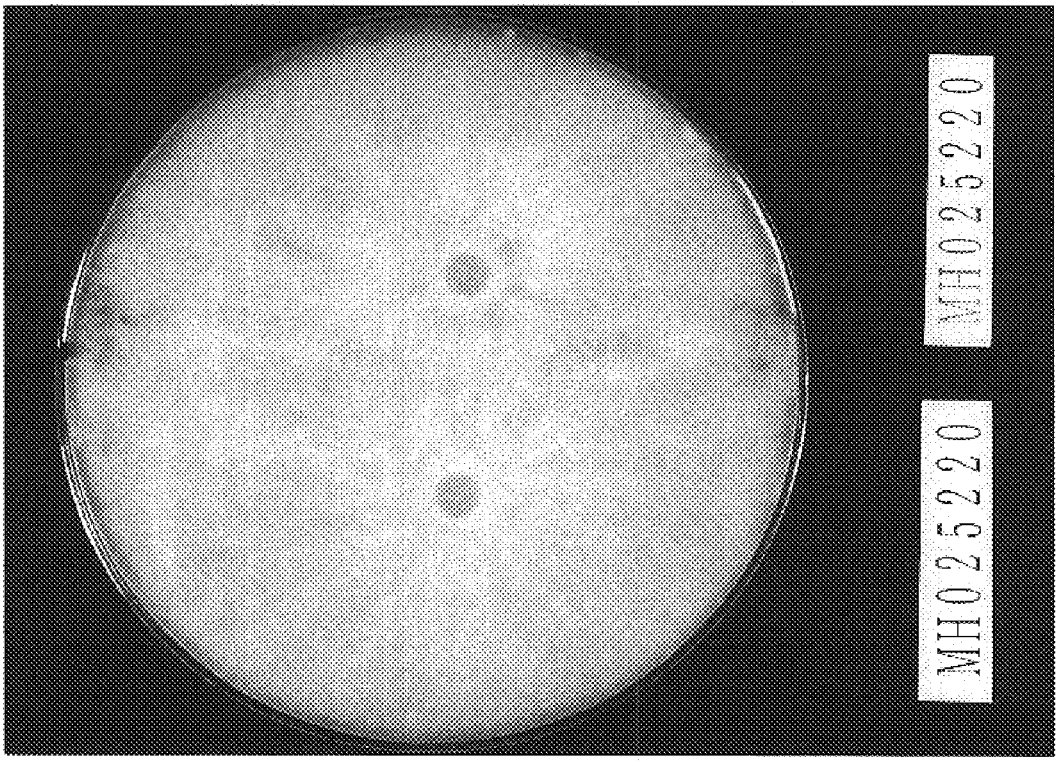
Figure 5:
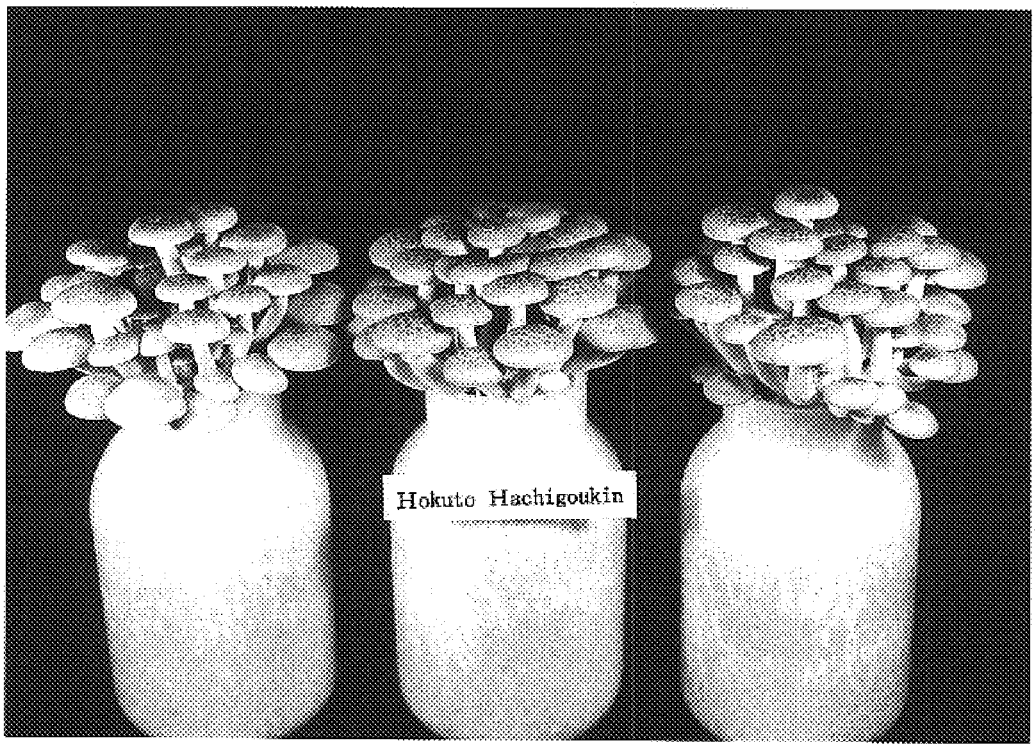
FIG. 5 is a photograph showing a front view of a parent plant variety, 'Hokuto Hachigoukin', cultivated in vases.
Figure 6A:
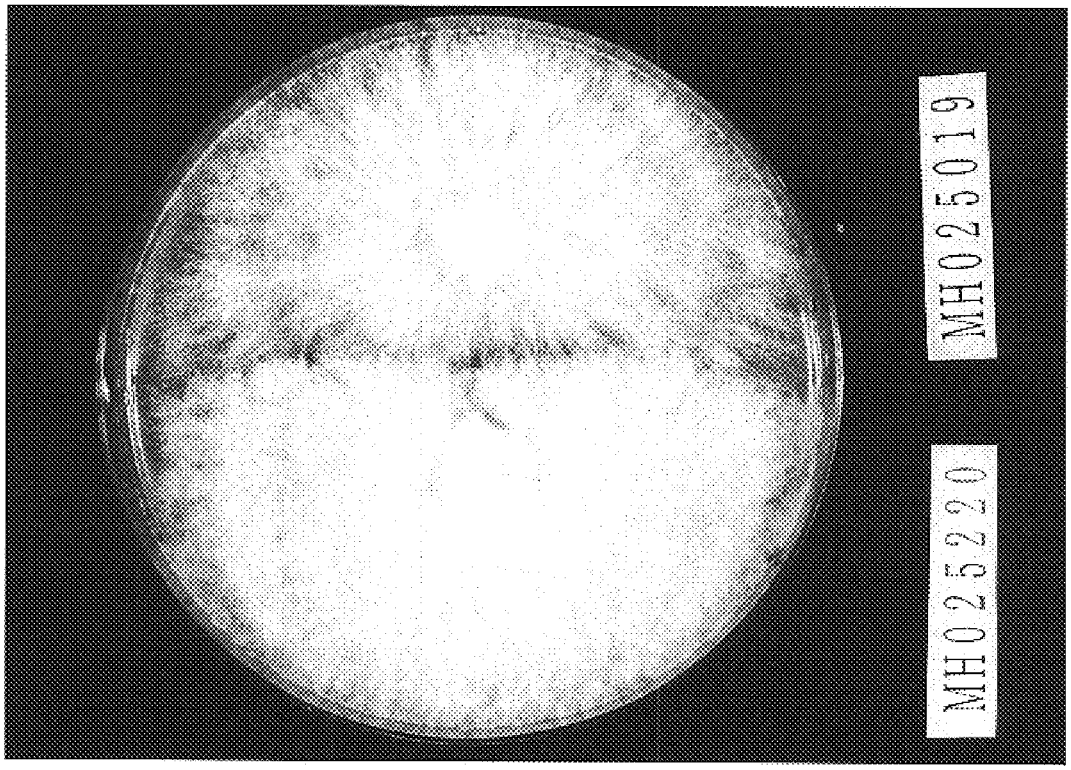
FIGS. 6A and 6B are photographs showing a surface and a back, respectively, of cultures of parent plant variety 'Hokuto Hachigoukin' (the inventor's company's internal designation being MH025019) and of the present invention (designation MH025220), grown in a single dish.
Figure 6B:
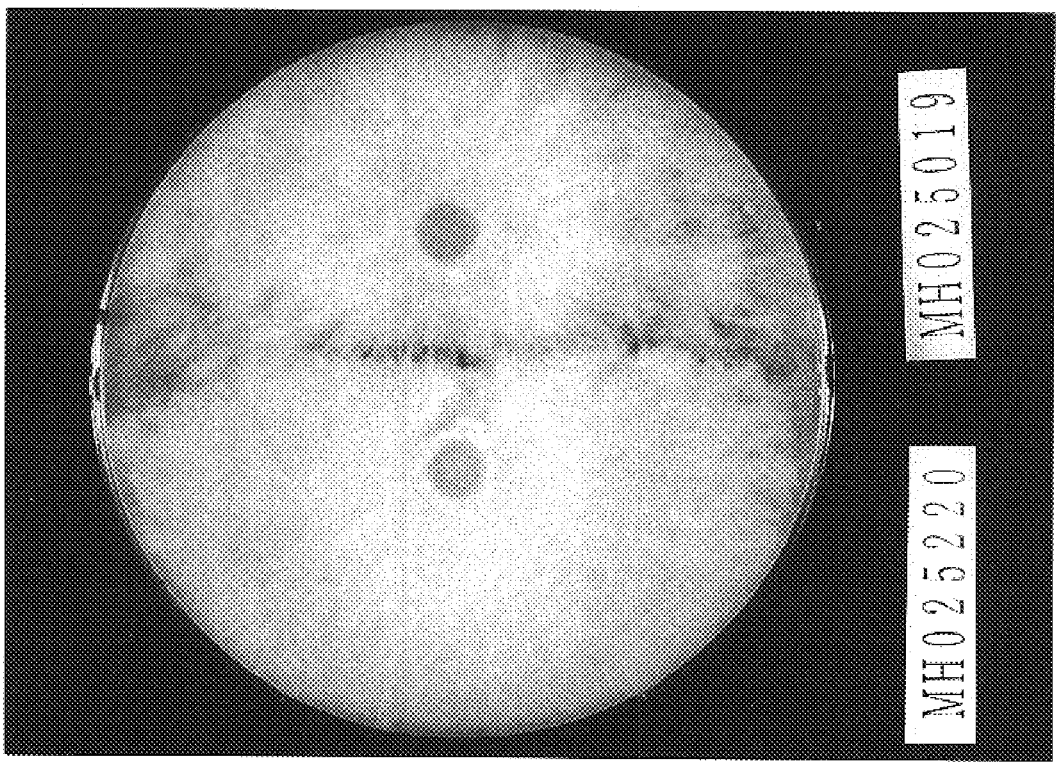
Figure 7:
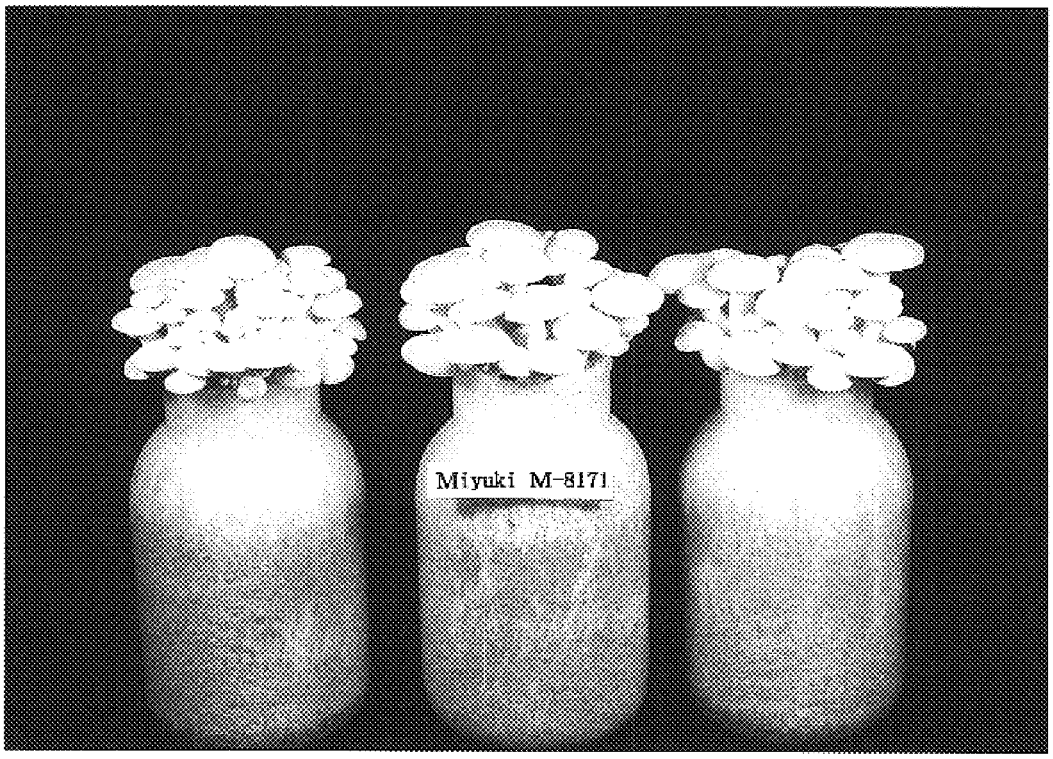
FIG. 7 is a photograph showing a front view of a comparison plant variety, 'Miyuki M-8171', cultivated in vases.
Figure 8A:
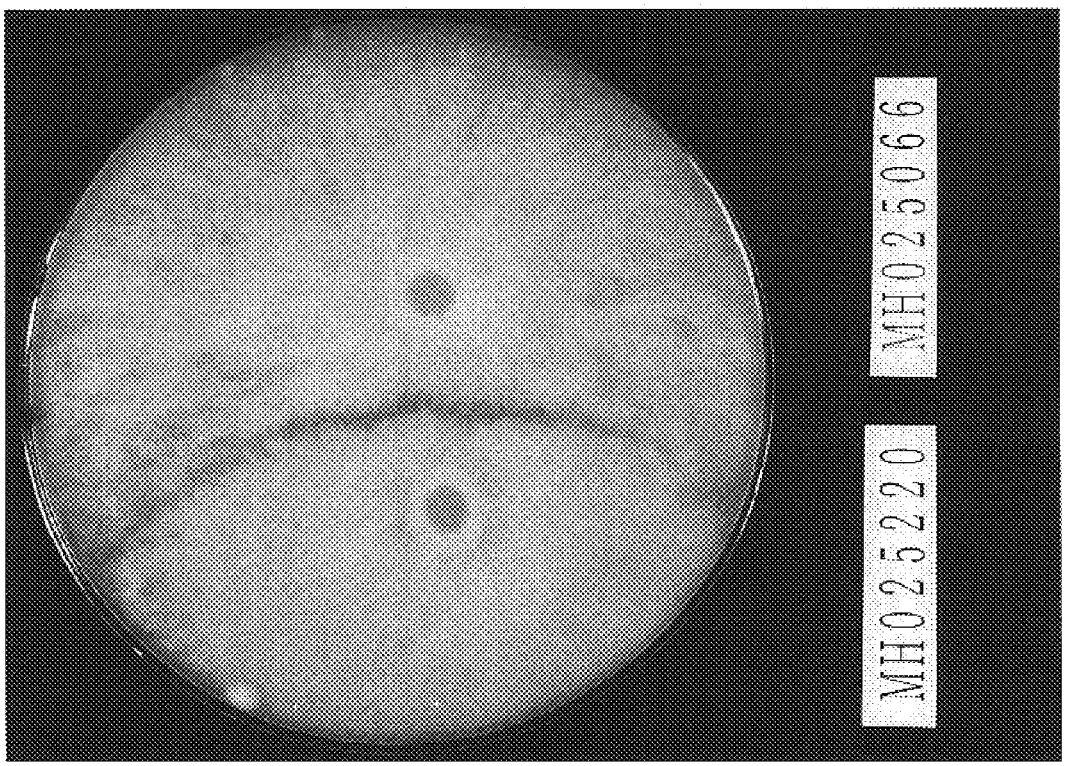
FIGS. 8A and 8B are photographs showing a top surface and a back surface, respectively, of cultures of plant varieties 'Miyuki M-8171' (the grower company's internal designation being MH025066) and of the present invention (internal designation MH025220), grown in a single dish.
Figure 8B:
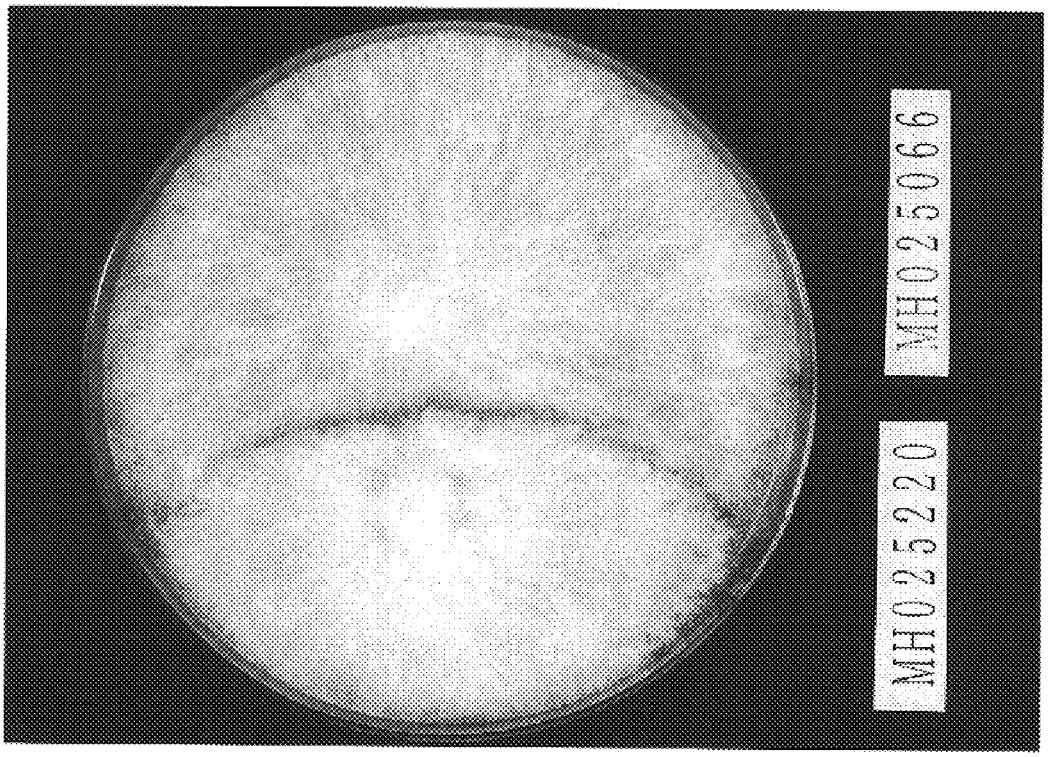
Figures 9A, 9B:
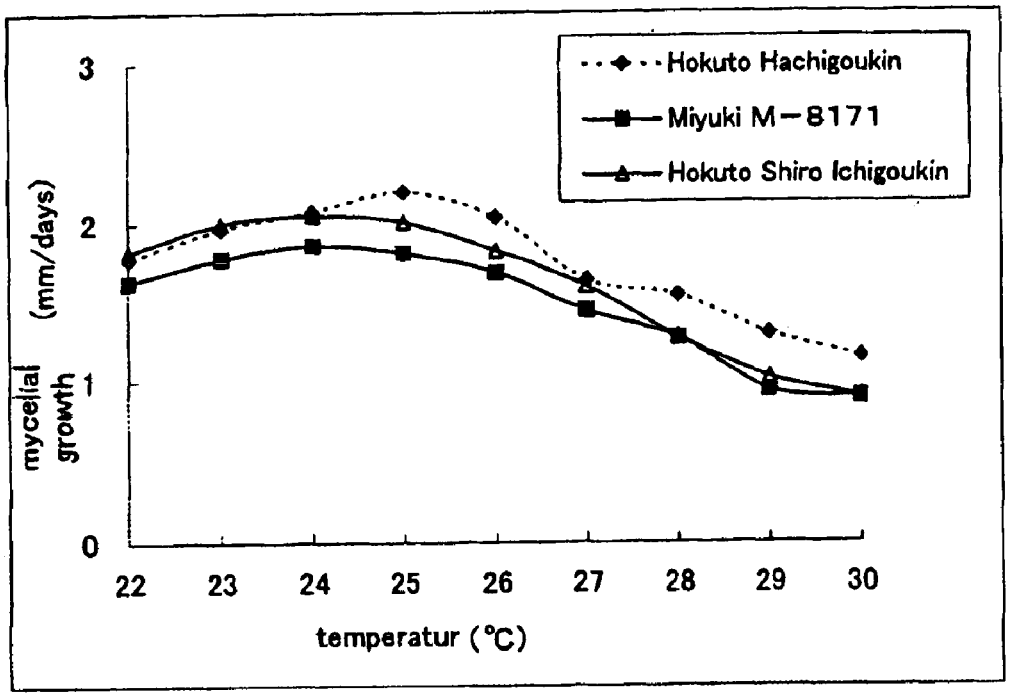
FIGS. 9A and 9B are a table and a graph, respectively, showing comparative mycelial growth of the present plant variety, as compared with that of parent plant variety 'Hokuto Hachigoukin' and comparison variety 'Miyuki M-8171'.

Photographs of the cultures for the present plant variety and for comparative varieties 'Hokuto Hachigoukin' and 'Miyuki M-8171' are shown on FIGS. 4, 6 and 8, respectively.

(2) Length of culture from spawning to fruit-body-formation promotion

The length of culture from spawning to fruit-body-formation promotion was investigated. Again, the test period was January–June 2002. Except for the number of cultivation days, cultivation was done according to the examination standards established for Shirotamogitake (*Hypsizygus ulmarius*). Three lengths of culture were established at 63, 70 and 77 days. The results are summarized in Table 2 below.

TABLE 2

| Culture Length | | |
|---|---|---|
| Culture length (days) | Growth length (days) | Yield (g/bottle) |
| 63 | 20.5 | 128.0 |
| 70 | 20.5 | 143.4 |
| 77 | 22.0 | 115.8 |

Based on the results shown in Table 2, the length of culture was set at 70 days because the yield was the highest for this length.

(3) Optimal budding temperature

To determine the optimal budding temperature, cultivation was done for 70 days according to the examination standards established for Shirotamogitake (*Hypsizygus ulmarius*). Three budding temperatures were established as shown in Table 3 below.

TABLE 3

| Optimal Budding Temperature | |
|---|---|
| Budding temperature (° C.) | Budding length (days) |
| 13~14 | 6.7 |
| 14~15 | 6.3 |
| 15~16 | 6.9 |

Based on the results shown in Table 3, the minimal temperature was set at 14–15° C. bacuase the length of budding was the shortest at this temperature.

(4) Optimal growth temperature

The optimal growth temperature was studied through cultivation for 70 days according to the examination standards established for Shirotamogitake (*Hypsizygus ulmarius*). Three growth temperatures were established as shown in Table 4 below.

TABLE 4

| Growth Temperature | | |
|---|---|---|
| Growth temperature (° C.) | Growth length (days) | Yield |
| 13~14 | 22.1 | 115.6 |
| 14~15 | 21.2 | 121.1 |
| 15~16 | 24.9 | 107.1 |

Based on the results shown in Table 4, the optimal growth temperature was set at 14–15° C. because the yield was the greatest at this temperature.

(5) Summary of cultivation characteristics

The cultivation characteristics of the present plant variety are shown in Table 5 below.

TABLE 5

| Summary of Cultivation Characteristics | | | |
|---|---|---|---|
| Characteristics | "Hokuto Shiro Ichigoukin" | "Hokuto Hachigoukin" | "Miyuki M-8171" |
| Length of culture from spawning to fruit-body-formation promotion (days) | 70 | 70 | 70 |
| Length of time from fruit-body-formation promotion to fruit body harvesting at optimal temperature (days) | 21 | 21 | 21 |
| Optimal budding temperature (° C.) | 14~15 | 14~15 | 14~15 |
| Fruit body development pattern | Clumped | Clumped | Group |
| Yield (g/bottle) | 118.5 | 117.1 | 105.1 |
| Number of effective fruit bodies | 62 | 100 | 79 |
| Medium compatibility | Sawdust | Sawdust | Sawdust |
| Tree selectivity | Mixture | Mixture | Mixture |
| Cap Size (Diameter) (mm) | 23.2 | 23.4 | 24.9 |
| Cross sectional shape | Umbonate | Umbonate | Umbonate |
| Center color | White | Yellowish brown | White |
| Margin color | White | Light grayish brown | White |

TABLE 5-continued

Summary of Cultivation Characteristics

| Characteristics | "Hokuto Shiro Ichigoukin" | "Hokuto Hachigoukin" | "Miyuki M-8171" |
|---|---|---|---|
| Meat thickness (cap depth) (mm) | 8.1 | 6.8 | 7.4 |
| Meat quality | Medium | Medium | Medium |
| Mottled spot quantity | Medium | Many | Medium |
| Mottled spot size | Medium | Medium | Medium |
| Mottled spot distribution | Central area | All areas except margin | All areas except margin |
| Mottled spot clarity | Medium | Medium | Medium |
| Cracking | Absent | Absent | Absent |
| Gills Color | Yellowish white | White | White |
| Arrangement | Orderly | Orderly | Wavy and frizzled |
| Width | Medium | Medium | Medium |
| Density | Medium | Medium | Medium |
| Stipe | | | |
| Length (mm) | | | |
| Attachment to cap | Centric: eccentric | Centric: eccentric | Centric: eccentric |
| Shape | Medium thick | Medium thick | Medium thick |
| Color | White | White | White |
| Hair | Absent | Absent | Absent |
| Ratio of maximum diameter to diameter just below mushroom cap | 1.59 | 1.58 | 1.72 |
| Ratio of length of mushroom stem to diameter just below mushroom cap | 2.1 | 2.45 | 1.68 |
| Meat quality | Medium | Medium | Medium |

The color designations are based on the Japan Color Standard for Horticultural Plant (JHS Color Chart). Other evaluations like the words "medium" are based on the standards stipulated by the Agriculture Forestry and Fisheries Ministry of Japan, under which strains may be evaluated with the eye.

(6) Cultivation characteristic data

Detailed cultivation characteristics of the present plant variety are shown in Table 6 below. The color designations are based on the Japan Color Standard for Horticultural Plant (JHS Color Chart). The code numbers mentioned in the column "Code of the similar variety" below are based on color codes stipulated by JIS (Japanese Industrial Standard). Other evaluations like the words "medium" are based on the standards stipulated by the Agriculture Forestry and Fisheries Ministry of Japan, under which strains may be evaluated with the eye.

TABLE 6

Detailed Cultivation Characteristics

| Characteristics | Characteristic code of filed variety | | | | | | | | |
|---|---|---|---|---|---|---|---|---|---|
| | 01 | 02 | 03 | 04 | 05 | 06 | 07 | 08 | 09 |
| Cultivation characteristics Length of culture from spawning to fruit-body-formation promotion (days) | 40 以下 | 41~50 | 51~60 | 61~70 | 71~80 | 81~90 | 91~100 | 101~110 | 111 以上 |

TABLE 6-continued

Detailed Cultivation Characteristics

| | | | | | | | | | |
|---|---|---|---|---|---|---|---|---|---|
| Length of time from fruit-body-formation promotion to fruit body harvesting at optimal temperature (days) | | | 19 以下 | | 20~25 | | 26 以上 | | |
| Optimal budding temperature (C.) | | 10 and under | 11~14 | 15~18 | 19~22 | 23~26 | 27 and over | | |
| Optimal developed temperature (C.) | | 8 and under | 9~11 | 12~14 | 15~17 | 18~20 | 21 and over | | |
| Optimal intensity | | | | | | | | | |
| Budding period | | | Early | | Iter-medi-ate | | Late | | |
| Fruiting habit | Grou-ped | Scat-tered | Clam-ped | | | | | | other |
| Yield (g/bottle) | | 80 以下 | | 81~100 | | 101~120 | | 121 以上 | |
| Number of effective fruit bodies | | 20 以下 | 21~25 | 26~30 | 31~35 | 36~40 | 41 以上 | | |
| Medium compa-tibility | Log wood | Saw-dust | | | | | | | other |
| Tree selectivity | Broad leved | Coni-ferour | mix-ture | | | | | | other |
| Morphology Cap Size | | | small | | medi-um | | large | | |
| Cross sectional shape | Conv ex | Umbo nate | expan ded | infund ibulife rm | | | | | other |
| Center color | W | GY | LG B | YB | GB | DY B | DGY B | DG B | other |
| Margin color | W | G–Y | LG B | YB | GB | DY B | DGY B | DG B | other |
| Thickness | | | Thin | | medi-um | | Thick | | |
| Hardness | | | Soft | | Medi-um | | Hard | | |
| Mottled spot quantity | | | Few | | Medi-um | | Many | | |
| Mottled spot size | | | small | | medi-um | | large | | |
| Mottled spot distribution | Cen-tral areas | All areas except mar-gin | | | | | | | other |
| Mottled spot clarity | | | uncle-ar | | medi-um | | Clear | | |

TABLE 6-continued

Detailed Cultivation Characteristics

| | | | | | | | | | |
|---|---|---|---|---|---|---|---|---|---|
| Cracking | Absent | | | | | | | | Present |
| Gills | | | | | | | | | |
| Color | W | YW | LOY | GY | | | | | other |
| Arrangement | Orderly | Sinuata | | | | | | | other |
| Width | | | Narrow | | Medium | | Wide | | |
| Density | | | Spaced | | Medium | | Dense | | |
| Stipe Length | | | Short | | Medium | | Long | | |
| Attachment to cap | Centric | Eccentric | | | | | | | Other |
| Shape | Thin Long | Thin Short | Thick Long | Thick Short | Medium Thick | | | | Other |
| Color | White | | | | | | | | Colored |
| Hair | Absent | | | | | | | | Present |
| Diameter under cap to maximum diameter ratio | | | 1.5 and under | | 1.6~1.8 | | 1.9 and over | | |
| Cap diameter to stipe length ratio | | | 1.4 and under | | 1.5~2.0 | | 2.1 and over | | |
| Hardness | | | Soft | | Medium | | Hard | | |
| Other characteristics | | | | | | | | | |
| Genetic Dual culture Inhibition zone | - | | | | | | | | + |
| Physiology Mycelial growth Effect of temperature The optimum (° C.) Growth rate | 22 | 23 | 24 | 25 | 26 | 27 | 28 | 29 | 30 |
| 5° C. | | | | | | | | | |
| 10° C. | | | | | | | | | |
| 15° C. | | | | | | | | | |
| 20° C. | | | | | | | | | |
| 25° C. | | | | | | | | | |
| 30° C. | | | | | | | | | |
| 35° C. | | | | | | | | | |

TABLE 6-continued

Detailed Cultivation Characteristics

| | | | | | | | |
|---|---|---|---|---|---|---|---|
| Mycelial density | | | Thin | | medium | Thick | |
| Development of aerial hyphae | | | Few | | medium | Many | |

| Characteristics | Code of the similar variety | | |
|---|---|---|---|
| | Note (Data) | Hokuto Hachigoukin | Miyuki M-817 |
| Cultivation characteristics Length of culture from spawning to fruit-body-formation promotion (days) | 70 days | 04 | 04 |
| Length of time from fruit-body-formation promotion to fruit body harvesting at optimal temperature (days) | 21 days | 05 | 05 |
| Optimal budding temperature ( C.) | 14–15 | 03, 04 | 03, 04 |
| Optimal developed temperature ( C.) | 14–15 | 04, 05 | 04, 05 |
| Optimal intensity | | | |
| Budding period | | | |
| Fruiting habit | Clumped | 03 | 01 |
| Yield (g/bottle) | 118.5 | 06 | 06 |
| Number of effective fruit bodies | 62.0 | 07 | 07 |
| Medium compatibility | Sawdust | 02 | 02 |
| Tree selectivity | Mixture | 03 | 03 |
| Morphology Cap Size | 23.2(mm) | 03 | 03 |
| Cross sectional shape | Umbonate | 02, 03 | 02 |
| Center color | White | 04 9YR1916 | 01 No4-01 |

TABLE 6-continued

| Detailed Cultivation Characteristics | | | |
|---|---|---|---|
| Margin color | White | 03 9YR1915 | 01 No4-01 |
| Thickness | 8.1(mm) | 05 | 05 |
| Hardness | Medium | 05 | 05 |
| Mottled spot quantity | ⊕ | 07 | 05 |
| Mottled spot size | ⊕ | 05 | 05 |
| Mottled spot distribution | Central area | 02 | 02 |
| Mottled spot clarity | Medium | 05 | 05 |
| Cracking | Absent | 01 | 01 |
| Gills | | | |
| Color | Yellowish white No.4-2501 | 01 | 01 |
| Arrange-ment | Orderly | 01 | 02 |
| Width | Medium | 05 | 05 |
| Density | Medium | 05 | 05 |
| Stipe Length | 49.3(mm) | 07 | 03 |
| Attachment to cap | Centric 7: eccentric 3 | 01 | 01 |
| Shape | Medium thick | 05 | 05 |
| Color | White | 01 | 01 |
| Hair | Absent | 01 | 01 |

TABLE 6-continued

| Detailed Cultivation Characteristics | | | |
|---|---|---|---|
| Diameter under cap to maximum diameter ratio | 1.59 | 03 | 05 |
| Cap diameter to stipe length ratio | 2.1 | 07 | 05 |
| Hardness | Medium | 05 | 05 |
| Other charac-teristics | | | |
| Genetic Dual culture Inhibition zone | 01 | 09 | 09 |
| Physiology Mycelial growth Effect of temperature The optimum (° C.) Growth rate | 24° C. | 04 | 03 |
| 5° C. | 4.0 mm/day | 4.9 | 6.4 |
| 10° C. | 9.3 mm/day | 12.2 | 13.7 |
| 15° C. | 19.9 mm/day | 18.7 | 20.5 |
| 20° C. | 25.8 mm/day | 24.3 | 26.3 |
| 25° C. | 28.6 mm/day | 30.6 | 31.2 |
| 30° C. | 11.6 mm/day | 15.5 | 16.9 |
| 35° C. | 0.8 mm/day | 2.6 | 1.2 |
| Mycelial density | Thick | 05 | 05 |
| Develop-ment of aerial hyphae | Medium | 03 | 05 |

In summary, the 'Hokuto Shiro Ichigoukin' is white in color and can be discriminated in variety by the boundary line seen when being cultivated in a dish with another different variety. By comparison, wild 'Bunashimeji Shirotamogitake' (*Hypsizygus ulmarius*) is not white. 'Hokuto Shiro Ichigoukin' tastes delicious when boiled.

What is claimed is:

1. A new and distinct variety of Bunashimeji mushroom plant as illustrated or described.

* * * * *

| temperature(℃) | 22 | 23 | 24 | 25 | 26 | 27 | 28 | 29 | 30 |
|---|---|---|---|---|---|---|---|---|---|
| Hokuto Shiro Ichigoukin | 1.81 | 2.00 | 2.05 | 2.01 | 1.83 | 1.60 | 1.28 | 1.02 | 0.90 |
| Hokuto Hachigoukin | 1.77 | 1.97 | 2.08 | 2.20 | 2.04 | 1.64 | 1.54 | 1.30 | 1.15 |
| Miyuki M−8171 | 1.63 | 1.78 | 1.86 | 1.81 | 1.69 | 1.45 | 1.27 | 0.94 | 0.90 |